(12) United States Patent
Hope et al.

(10) Patent No.: US 6,410,812 B1
(45) Date of Patent: Jun. 25, 2002

(54) PROCESS FOR RECOVERING BORON TRIFLUORIDE FROM A CATALYST COMPLEX

(75) Inventors: Kenneth D. Hope; Ting C. Ho, both of Kingwood, TX (US); David L. Archer, Decatur, AL (US); Russell J. Bak, The Woodlands, TX (US); J. Barry Collins, New Caney, TX (US); Doug W. Burns, Kingwood, TX (US)

(73) Assignee: Chevron Phillips Chemical Company LP, Houston, TX (US)

( * ) Notice: Subject to any disclaimer, the term of this patent is extended or adjusted under 35 U.S.C. 154(b) by 0 days.

(21) Appl. No.: 09/516,578

(22) Filed: Mar. 1, 2000

(51) Int. Cl.[7] ............................. C07C 2/08; C07C 7/00
(52) U.S. Cl. ..................... 585/525; 585/800; 585/904; 585/906
(58) Field of Search ................ 585/525, 800, 585/904, 906

(56) References Cited

U.S. PATENT DOCUMENTS

| | | | | |
|---|---|---|---|---|
| 2,167,358 A | | 7/1939 | Gleason ..................... 423/284 |
| 4,956,512 A | | 9/1990 | Nissfolk et al. ............. 585/521 |
| 4,982,042 A | * | 1/1991 | Akatsu et al. ............... 585/510 |
| 5,191,140 A | * | 3/1993 | Akatsu et al. ............... 585/525 |
| 5,254,784 A | | 10/1993 | Nurminen et al. ........... 585/525 |
| 5,705,727 A | * | 1/1998 | Holub et al. ................. 585/525 |
| 5,811,616 A | * | 9/1998 | Holub et al. ................. 585/504 |
| 5,994,605 A | * | 11/1999 | Bak et al. .................... 585/525 |

FOREIGN PATENT DOCUMENTS

| | | | | |
|---|---|---|---|---|
| EP | 0594065 B1 | 10/1988 | ............ B01J/27/32 |
| EP | 0364815 | 10/1989 | ........... C07C/7/152 |
| EP | 0742191 B1 | * | 7/1999 | |

* cited by examiner

Primary Examiner—Walter D. Griffin
(74) Attorney, Agent, or Firm—Williams, Morgan & Amerson, P.C.

(57) ABSTRACT

In a process for the oligomerization of alpha olefins using a boron trifluoride/alcohol catalyst complex a method for recovering the boron trifluoride from the product stream which comprises lowering the pressure of the product stream to flash off excess boron trifluoride, mixing the boron trifluoride with fresh alcohol to form fresh boron trifluoride/alcohol catalyst complex, and introducing the fresh catalyst back into the oligomerization reactor.

19 Claims, 1 Drawing Sheet

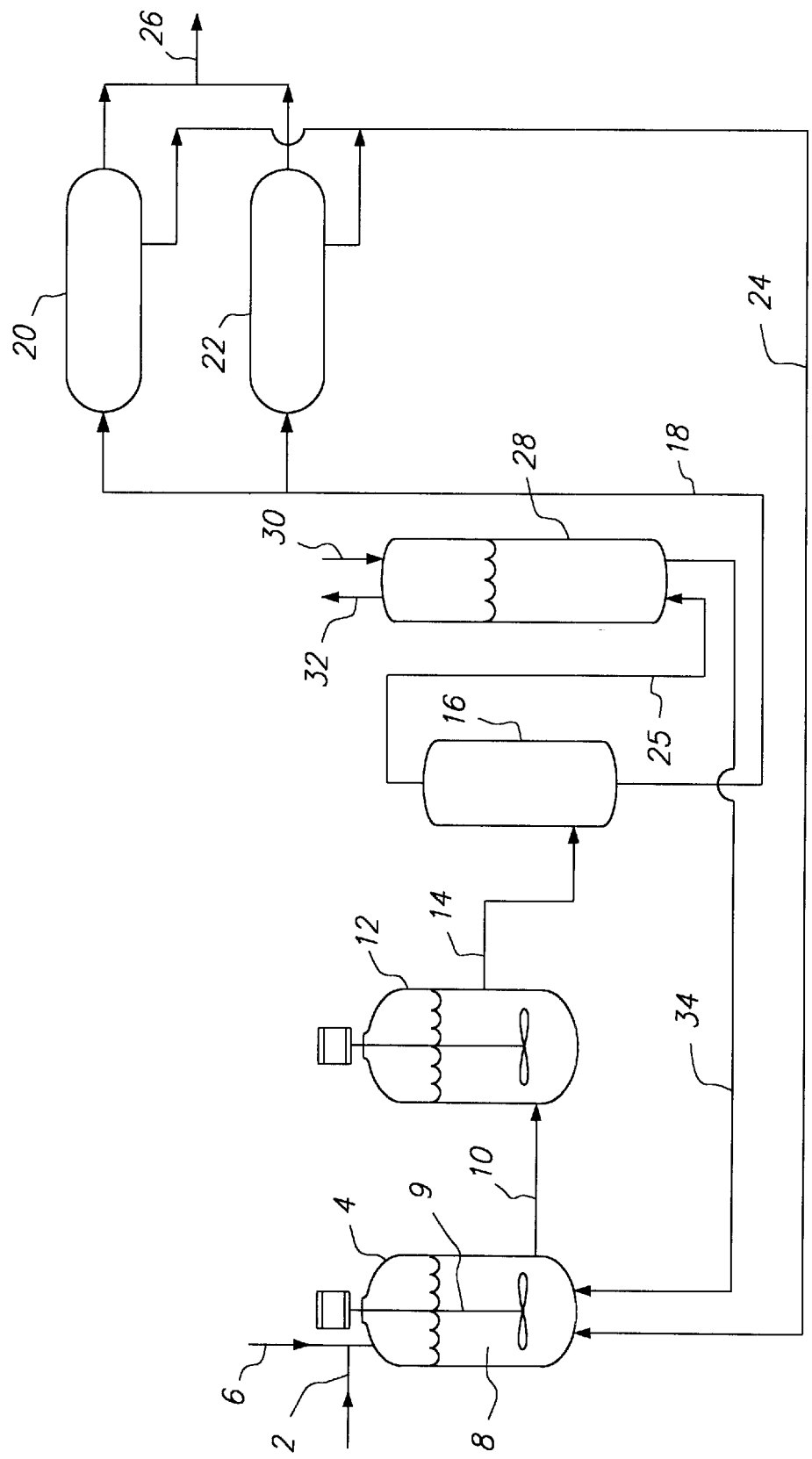

PROCESS FOR RECOVERING BORON TRIFLUORIDE FROM A CATALYST COMPLEX

FIELD OF THE INVENTION

The present invention relates to a process for recovering at least a portion of the boron trifluoride ($BF_3$) present in a catalytic mixture comprising $BF_3$/alcohol catalyst complex used as a promoter in an oligomerization process for alpha olefins.

BACKGROUND OF THE INVENTION

Boron trifluoride is the catalyst of choice for producing polyalphaolefins (PAO) of varying viscosity grades. See for example U.S. Pat. Nos. 4,956,512 and 5,945,574. Boron trifluoride is a gas which is usually combined with a protic promoter, typically an alcohol such as butanol, to form a catalyst complex which may be used to promote the oligomerization of alpha olefins, such as for example 1-decene or 1-dodecene. The boron trifluoride represents a significant cost in process schemes for producing polyalphaolefins. Furthermore, since used catalyst is often disposed of by deep-well injection in commercial operations producing polyalphaolefins, the disposal of the used catalyst has some environmental considerations.

Various methods for recovering the boron trifluoride have been proposed. See for example U.S. Pat. No. 2,167,358 which uses a trivalent nitrogen compound to form a complex with the boron trifluoride. U.S. Pat. No. 5,846,429 teaches the adsorption of the boron trifluoride on a synthetic polymer containing a nitrile group and then recovering the boron trifluoride by heating the polymer fibers. Other methods for recovering the boron trifluoride include thermally cracking the boron trifluoride complex (European Patent Application 96303173.7) and recovering the boron trifluoride as a hydrate (European Patent Application 89118395.6). U.S. Pat. No. 5,254,784 describes a method for recovering excess boron trifluoride from the boron trifluoride/alcohol complex without decomposition of the complex by distilling the reaction product under reduced pressure, recovering the excess boron trifluoride as an exhaust gas, forming additional complex by using alcohol as the liquid ring or fluid moment in either a liquid pump or a torque pump, and recycling the complex to the reactor.

Unfortunately none of the processes described in the prior art have been proven to be practical in commercial operations for the oligomerization of alpha olefins. The present invention is directed to a practical method for recovering boron trifluoride from a product stream, combining the recovered boron triflouride with a protic promoter, and introducing the fresh mixture into the reactor. Pilot plant studies have demonstrated that the process scheme of the present invention significantly increases the efficiency of the process.

SUMMARY OF THE INVENTION

In its broadest aspect, the present invention is directed to a method for separating at least part of the boron trifluoride present in a mixture comprised of boron trifluoride and an alcohol having from 1 to about 10 carbon atoms, wherein excess boron trifluoride is present in the mixture than used to form a complex of boron trifluoride and alcohol, the method comprising (a) reducing the pressure of the mixture sufficiently to cause the separation of boron trifluoride vapor from a liquid organic phase which Includes boron trifluoride/alcohol complex; (b) recovering the boron trifluoride vapor separately from the liquid organic phase; and (c) mixing the boron trifluoride vapor from step (b) with fresh alcohol using countercurrent flow to form additional boron trifluoride/alcohol complex. This method is particularly useful in a process which utilizes the boron trifluoride/alcohol complex as a catalyst in a reaction zone for the oligomerization of alpha olefins.

The present invention is further directed to a process scheme for the oligomerization of an apha-olefin in the presence of boron trifluoride catalyst which comprises (a) contacting in an oligomerization zone an alpha olefin feed with a catalytic mixture comprising an effective catalytic amount of a catalyst complex consisting of boron trifluoride and a protic promoter under conditions and for a time sufficient to oligomerize the alpha olefins in the feed whereby a liquid organic mixture is formed comprising polyalphaolefins and the catalytic mixture; (b) recovering the liquid organic mixture from the oligomerization zone; (c) reducing the pressure of the liquid organic mixture recovered in step (b) sufficiently to separately recover a gas comprising at least a portion of the boron trifluoride present in the catalytic mixture and a liquid product stream comprising the polyalphaolefin product and residual catalyst complex; (d) mixing the gaseous boron trifluoride recovered from step (c) with fresh protic promoter to form fresh catalyst and promoter mixture; (e) introducing the fresh catalyst complex from step (d) into the oligomerization zone of step (a); and (f) recovering the polyalphaolefin product from the liquid product stream of step (c). In a preferred embodiment of the process scheme, the residual catalyst complex is also recovered separately from the polyalphaolefin product in step (f) above and is recycled back to the oligomerization zone of step (a).

The protic promoter forms a catalyst complex with the boron trifluoride, and the complex serves as a catalyst for the oligomerization of alpha olefins. The protic promoter will usually be an alcohol having from 1 to about 10 carbon atoms in the molecule. Preferably the protic promoter is n-butanol. The catalytic mixture comprising the boron trifluoride/alcohol complex usually also contains excess boron trifluoride which is adsorbed in the mixture. It is primarily the excess boron trifluoride which is recovered by the method described herein.

The alpha olefin feed will generally comprise an alpha olefin or a mixture of alpha olefins having from about 6 to about 20 carbon atoms in the molecule. In one preferred embodiment of the invention, the alpha olefin feed will comprise decene or a mixture of alpha olefins containing decene. In carrying out the process scheme when n-butanol is the protic promoter, the pressure in the oligomerization zone is preferably maintained at 40 psig or greater. In recovering the boron trifluoride from the catalytic mixture, the pressure is preferably reduced to at least 2.0 psia or lower and more preferably will be reduced to 0.1 psia or less. However one skilled in the art will recognize that the optimal pressure in the oligomerization zone and also used for the recovery of the boron trifluoride may vary somewhat depending on the protic promoter employed. However, finding the optimal conditions for carrying out the process with the various operable protic promoters should involve only routine testing.

A particular advantage of the present invention is that a much smaller absorbing vessel for the preparation of the catalyst complex may be used than would otherwise be necessary when a conventional Schott reactor is employed. The smaller absorbing vessel makes it possible to accelerate the time required to reach a steady state in the vapor absorber. The process of the present invention also significantly increases the efficiency of the boron trifluoride catalyst.

As used in this disclosure the phrase "effective catalytic amount" refers the amount of catalyst necessary to promote the polymerization of the alpha olefin or mixture of alpha olefins present in the feed.

As used in this disclosure the words "comprises" or "comprising" is intended as an open-ended transition meaning the inclusion of the named elements, but not necessarily excluding other unnamed elements. The phrase "consists essentially of" or "consisting essentially of" is intended to mean the exclusion of other elements of any essential significance to the combination. The phrase "consisting of" is intended as a transition meaning the exclusion of all but the recited elements with the exception of only minor traces of impurities.

BRIEF DESCRIPTION OF THE DRAWINGS

The FIGURE is a schematic representation of a process scheme which represents one embodiment of the present invention.

DETAILED DESCRIPTION OF THE INVENTION

The present invention may be more clearly understood by referring to the FIGURE which illustrates one embodiment of the invention. In the FIGURE an alpha olefin feedstream 2, preferably consisting essentially of decene, enters the first oligomerization reactor 4. Fresh boron trifluoride gas enters the reactor via conduit 6. The reactor contains a liquid organic mixture 8 comprising boron trifluoride/alcohol catalyst complex, alpha olefin monomer, and polyalphaolefin, as well as excess boron trifluoride adsorbed in the mixture. As noted above, a number of different alcohols may be used in forming the catalyst complex that serves to catalyze the oligomerization reaction of the alpha olefins, but the preferred alcohol for carrying out the present invention is n-butanol. A stirrer 9 aids in mixing the liquid and the gaseous boron trifluoride and to facilitate the oligomerization reaction. The liquid organic mixture is carried by conduit 10 to a second reactor 12 were additional oligomerization of the alpha olefins occurs. Reactors 4 and 12 are preferably maintained at superatmospheric pressure and more preferably are maintained at a pressure of 40 psig or above. From the second reactor 12 the liquid organic mixture is carried via line 14 to flash drum 16 in which the pressure is reduced sufficiently to flash off at least a portion of the boron trifluoride present in the liquid organic mixture. Preferably the pressure of the liquid organic mixture is reduced in the flash drum to 2.0 psia or below and more preferably the pressure is reduced to 0.1 psia or less. A liquid product stream is recovered from the flash drum by conduit 18 and carried to the two parallel coalescers 20 and 22, respectively, where residual boron trifluoride/butanol complex and unreacted alpha olefin monomer are collected and returned to the first reactor 4 via line 24. The polyalphaolefin product is recovered from the coalescers by line 26. Returning to the flash drum 16, boron trifluoride vapor and inert gases, such as nitrogen, are recovered by line 25 and carried to vapor scrubber 28 which serves as the absorbing vessel. In the vapor scrubber the mixture of boron trifluoride vapor and inert gases is passed in a countercurrent direction through fresh butanol which is introduced into the vapor scrubber by inlet 30. The inert gases which were also recovered in the flash drum are removed from the vapor scrubber via outlet 32. The boron trifluoride and butanol form fresh catalyst complex which is carried to the first reactor 4 via line 34.

In conventional process schemes the liquid organic mixture is carried directly from the reactors to the coalescers. In some schemes the catalyst complex recovered from the coalescers is recycled to the reactor in the manner shown by line 24 in the FIGURE. Unfortunately, commercial operating experience has demonstrated that due to chemical changes in the recycled catalyst complex, the effectiveness of the catalyst in promoting the oligomerization reaction is significantly reduced. In order to make up for the lost catalytic activity, in a conventional scheme fresh catalyst complex is usually prepared in a an absorber (not shown in the FIGURE, since it is not necessary with the present invention) and is introduced separately into the reactor. In the embodiment shown in the FIGURE, the vapor scrubber takes the place of the conventional absorber. The present invention is significantly more efficient than conventional processing schemes and makes possible a reduction in the amount of boron trifluoride consumed during operation. Pilot plant trials of the present invention have shown as much as a 35% reduction in the amount of boron trifluoride consumed as compared to baseline trials using conventional process schemes not using the flash drum and vapor scrubber.

The vapor scrubber as illustrated in the FIGURE and as used in the pilot plant studies discussed below is a fixed-bed, counter-current, vapor-liquid contact apparatus. The pilot plant studies showed that the vapor scrubber efficiently separated boron trifluoride from the inert components. In addition, the use of the flash drum and the vapor scrubber employed in the recycling scheme of the present invention showed significant improvement in catalyst efficiency, both when used by itself and when used in conjunction with the catalyst complex coalescing equipment as shown in the FIGURE. When compared to a once through (no-recycle) mode, the vapor scrubber used in conjunction with a coalescer was found to improve the catalyst efficiency by over 60% under quasi-optimal experimental conditions.

Experiments have confirmed that boron trifluoride vapor collected from the product flash drum can be absorbed with fresh butanol to form "reformulated boron trifluoride/butanol complex". The reformulated catalyst complex can then be recycled to the first reactor to promote the oligomerization of the alpha olefins. As compared to a conventional processing scheme in which there is no boron trifluoride recovery, a 39% to 47% improvement in catalyst efficiency was realized in the continuous pilot plant operated according to the present invention.

The absolute pressure (degree of vacuum) in the flash drum is important in optimizing the recovery of boron trifluoride vapor from the product stream. At a pressure of 2 psia in the flash drum the recovery of boron trifluoride is calculated to be about 80% or greater. It is expected that maximum recovery will be achieved at a flash tank pressure of about 0.1 psia. In order to carry out the process of the invention in the most advantageous manner, it is desirable to operate the oligomerization reactor or reactors at a somewhat higher pressure than has normally been commercially practiced. In conventional process schemes, the oligomerization reactors are usually maintained at a pressure between about atmospheric pressure up to about 30 psig. In the case of the present invention the oligomerization reactors are preferably maintained at a pressure of at least 40 psig.

The invention may be further illustrated by the following examples. While the examples are provided to help illustrate the present invention, they are not intended to limit it.

EXAMPLE 1

The pilot plant was operated in a once-through mode, i.e., with no boron trifluoride recovery and recycle. The reactor pressure was maintained at 40 psig. During this run an average of 28.5 gallons of polyalphaolefin product (PAO) was produced for each pound of boron trifluoride ($BF_3$) consumed (GPP). This example was used as the base case in order to evaluate catalyst efficiency, which for the purpose of comparison with the following examples is defined as the percent change of GPP of $BF_3$ consumption as compared to that of the base run average (28.5 GPP).

EXAMPLE 2

The processing scheme as in Example 1 was conducted in the pilot plant with the exception of the reactor pressure which was maintained at 60 psig $BF_3$. The results of the run and a comparison with the other examples in this application are shown in the Table below.

EXAMPLE 3

The processing scheme as in Example 1 was conducted in the pilot plant with the exception of the reactor pressure which was maintained at 80 psig $BF_3$. The results of the run and a comparison with the other examples in this application are shown in the Table below.

EXAMPLE 4

The pilot plant was modified to accommodate a flash drum and a $BF_3$ vapor scrubber as described in the FIGURE. Fresh n-butanol was used as the protic promoter and flowed counter-current to the vapor stream from the flash tank. The vapor scrubber employed in the pilot plant was a vertically positioned glass tube filled with "Teflon" spheres which helped to reduce the liquid retention volume (residence time) in the vapor scrubber. A predetermined amount of fresh butanol was injected into the bottom of the vapor scrubber, while a controlled amount of $BF_3$-rich liquid was removed from the top of vapor scrubber. A steady state operation was achieved by maintaining a constant liquid level in the vapor scrubber. The vent gas stream from the vapor scrubber was bubbled through a flask of ethylene glycol. The ethylene glycol solution was constantly monitored for possible weight gain (which indicated incomplete $BF_3$ absorption in the vapor scrubber). In this manner it was possible to optimize the absorption of the $BF_3$.

Except for the addition of the flash drum and the vapor scrubber, the oligomerization was carried out as in Example 1. The flash drum was maintained under high vacuum (0.1 psia). As shown in the following Table, the catalyst efficiency was greatly improved by the use of the flash drum and vapor scrubber. Over several runs a catalyst efficiency of 40–43 GPP was observed; this was equivalent to an increase in efficiency of 39–47% as compared to the base run (Example 1 above).

EXAMPLE 5

The processing scheme as in Example 4 was conducted in the pilot plant with the exception of the reactor pressure which was maintained at 60 psig $BF_3$. The results of the run and a comparison with the other examples in this application are shown in the Table below.

EXAMPLE 6

The processing scheme as in Example 4 was conducted in the pilot plant with the exception of the reactor pressure which was maintained at 80 psig $BF_3$. The results of the run and a comparison with the other examples in this application are shown in the Table below.

EXAMPLE 7

The processing scheme as in Example 4 was conducted in the pilot plant with the exception of the flash tank pressure which was maintained at 14 psia. The results of the run and a comparison with the other examples in this application are shown in the Table below.

TABLE

CATALYST EFFICIENCY COMPARED WITHOUT $BF_3$ VAPOR RECOVERY AND WITH $BF_3$ VAPOR RECOVERY

| | Cat. Efficiency (gal PAO/#$BF_3$) | |
|---|---|---|
| Continuous Run Data | Avg | Percent Change |
| 1  1(a) No Recovery w/rx @ 40 psig | 28.53 | Base |
| 2  (1b) No recovery w/rx @ 60 psig | 27.39 | |
| 3  (1c) No recovery w/rx @ 80 psig | 21.84 | |
| 4  (4a) Scrubber (LP[1]) w/rx @ 40 psig | 41.88 | 46.8 |
| 5  (4b) Scrubber (LP[1]) w/rx @ 60 psig | 39.68 | 39.1 |
| 6  (4c) Scrubber (LP[1]) w/rx @ 80 psig | 37.52 | 31.5 |
| 7  (4d) Scrubber (HP[2]) w/rx @ 40 psig | 31.23 | 9.5 |

[1]Flash Tank at 0.1 psia
[2]Flash Tank at 14 psia

The data in the Table clearly illustrate the advantage of practicing the recovery of the boron trifluoride according to the present invention as compared to conventional processing schemes. The efficiency of the boron triflouride/butanol system showed a significant increase when the flash drum and vapor absorber were incorporated into the process scheme. The importance of reducing the pressure in the flash drum is also shown by comparing the data in Example 7 to that in Examples 4, 5, and 6. While still operable at a flash drum pressure of 14 psia, the improvement in efficiency of the catalyst complex as compared to the base case was only 9.5% while the other examples showed improvements in the range of 30 to 40%. Under the conditions of the pilot plant tests the optimal reactor pressure for carrying out the process of the invention was between about 40 psig and about 60 psig.

What is claimed is:

1. A process scheme for the oligomerization of an alpha-olefin in the presence of boron trifluoride catalyst which comprises:

(a) contacting in an oligomerization zone an alpha olefin feed with a catalytic mixture comprising an effective catalytic amount of a catalyst complex consisting of boron trifluoride and a protic promoter under conditions and for a time sufficient to oligomerize the alpha olefins in the feed whereby a liquid organic mixture is formed comprising a polyalphaolefin product and the catalytic mixture;

(b) recovering the liquid organic mixture from the oligomerization zone;

(c) reducing the pressure of the liquid organic mixture recovered in step (b) sufficiently to separately recover (i) a gas comprising at least a portion of the boron trifluoride present in the catalytic mixture and at least a portion of inert gas present in the liquid organic mixture, and (ii) a liquid product stream comprising the polyalphaolefin product and residual catalyst complex;

(d) mixing the gaseous boron trifluoride recovered from step (c) with fresh protic promoter to form fresh catalyst and promoter mixture, wherein the catalyst and promoter mixture is substantially free of the inert gas;

(e) introducing the fresh catalyst and promoter mixture from step (d) into the oligomerization zone of step (a); and (f) recovering the polyalphaolefin product from the liquid product stream of step (c).

2. The process scheme of claim 1 which also includes separately recovering in step (f) the residual catalyst complex present in the liquid product stream and recycling the residual catalyst complex back into the oligomerization zone of step (a).

3. The process scheme of claim 1 wherein the protic promoter is an alcohol having from 1 to about 10 carbon atoms in the molecule.

4. The process scheme of claim 3 wherein the alcohol is n-butanol.

5. The process scheme of claim 3 wherein the pressure in the oligomerization zone is 40 psig or greater and the pressure of the liquid organic mixture is reduced to less than 2 psia.

6. The process scheme of claim 5 wherein the pressure of the liquid organic mixture is reduced to 0.1 psia or less.

7. The process scheme of claim 1 wherein step (c) is carried out in a vacuum flash tank.

8. The process scheme of claim 1 wherein step (d) is carried out in a counter current gas-liquid mixing apparatus.

9. The process of claim 1 wherein the alpha olefin feed comprises an alpha olefin or a mixture of alpha olefins having from about 6 to about 20 atoms in the molecule.

10. The process of claim 9 wherein the alpha olefin feed comprises decene or a mixture of alpha olefins which include decene.

11. A method for separating at least part of the boron trifluoride present in a mixture comprised of boron trifluoride, inert gas, and an alcohol having from 1 to about 10 carbon atoms, wherein excess boron trifluoride is present in the mixture than used to form a complex of the boron trifluoride and alcohol, the method comprising:

(a) reducing the pressure of the mixture sufficiently to cause the separation of boron trifluoride vapor and inert gas from a liquid organic phase which includes boron trifluoride/alcohol complex;

(b) recovering the boron trifluoride vapor separately from the liquid organic phase; and (c) mixing the boron trifluoride vapor from step (b) with fresh alcohol using countercurrent flow to form additional boron trifluoride/alcohol complex, wherein the boron trifluoride/alcohol complex is substantially free of the inert gas.

12. The method of claim 11 wherein the liquid organic phase also includes polyalphaolefins in addition to the boron trifluoride/alcohol complex.

13. The method of claim 12 wherein the boron trifluoride/alcohol complex serves as a catalyst in a reaction zone for the oligomerization of alpha olefins.

14. The method of claim 13 wherein the boron trifluoride alcohol complex formed in step (c) is introduced into the reaction zone.

15. The method of claim 13 wherein the reaction zone is maintained at a pressure of at least 40 psig and the pressure during step (a) is no more than 2 psia.

16. The method of claim 15 wherein the pressure during step (a) is no more than 0.1 psia.

17. The method of claim 11 wherein the alcohol is n-butanol.

18. A process for oligomerizing alpha olefins in the presence of a boron trifluoride/alcohol catalyst complex which comprises:

(a) contacting in an oligomerization zone an alpha olefin feed comprising an alpha olefin or a mixture of alpha olefins having from about 10 to about 12 carbon atoms in the molecule with a catalytic mixture comprising an effective catalytic amount of boron trifluoride/alcohol catalyst complex and excess boron trifluoride under conditions and for a time sufficient to promote the oligomerization of the alpha olefins, wherein the alcohol in the catalytic mixture contains from 1 to about 10 carbon atoms in the molecule and the pressure in the oligomerization zone is maintained at about 40 psig or greater;

(b) recovering a liquid organic mixture comprising polyalphaolefin product, boron trifluoride/alcohol catalyst complex, excess boron trifluoride, inert gas, and unreacted alpha olefin from the oligomerization zone;

(c) reducing the pressure of the liquid organic mixture recovered in step (b) to about 2 psig or less;

(d) recovering boron trifluoride vapor and inert gas separately from a liquid product stream comprising polyalphaolefin product, unreacted alpha olefins, polyalphaolefin product, and boron trifluoride/alcohol catalyst complex;

(e) recovering the polyalphaolefin product separately from a recycle mixture comprised of unreacted alpha olefin and boron trifluoride/alcohol catalyst complex;

(f) returning the recycle mixture of step (e) to the oligomerization zone;

(g) mixing the boron trifluoride vapor recovered in step (d) with fresh alcohol whereby fresh catalyst complex is formed, wherein the fresh catalyst complex is substantially free of the inert gas; and (h) introducing the fresh catalyst complex from step (g) into the oligomerization zone.

19. The process of claim 18 wherein the alcohol in the catalyst complex is n-butanol.

* * * * *